US00PP24443P2

(12) United States Plant Patent
Head et al.

(10) Patent No.: US PP24,443 P2
(45) Date of Patent: May 13, 2014

(54) ***BUXUS* PLANT NAMED 'RLH-BI'**

(50) Latin Name: ***Buxus microphylla* var. *koreana***
Varietal Denomination: RLH-BI

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: Head's Select Inc., Seneca, SC (US)

( * ) Notice: Subject to any disclaimer, the term of this patent is extended or adjusted under 35 U.S.C. 154(b) by 0 days.

(21) Appl. No.: 13/573,611

(22) Filed: Sep. 27, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — C. A. Whealy

(57) ABSTRACT

A new and distinct cultivar of *Buxus* plant named 'RLH-BI', characterized by its compact, outwardly spreading to decumbent, billowy and mounding plant habit; vigorous growth habit; moderately rapid growth rate; freely branching habit; flexible lateral branches that are resistant to cracking and splitting; bright green-colored developing leaves that become dark green with development; and good winter hardiness.

1 Drawing Sheet

Botanical designation: *Buxus microphylla* var. *koreana.*
Cultivar denomination: 'RLH-BI'.

BACKGROUND OF THE INVENTION

The present invention relates to a new and distinct cultivar of *Buxus* plant, commercially referred to as Boxwood, botanically known as *Buxus microphylla* var. *koreana* and hereinafter referred to by the name 'RLH-BI'.

The new *Buxus* plant is a naturally-occurring branch mutation of *Buxus microphylla* var. *koreana* 'Kingsville', not patented. The new *Buxus* plant was discovered and selected by the Inventors in 1991 on a single plant of 'Kingsville' in a controlled outdoor nursery environment in Long Creek, Oconee County, S.C.

Asexual reproduction of the new *Buxus* plant by semi-hardwood and hardwood cuttings in a controlled environment in Long Creek, Oconee County, S.C. since 1996 has shown that the unique features of this new *Buxus* plant are stable and reproduced true to type in successive generations.

SUMMARY OF THE INVENTION

Plants of the new *Buxus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'RLH-BI'. These characteristics in combination distinguish 'RLH-BI' as a new and distinct *Buxus* plant:

1. Compact, outwardly spreading to decumbent, billowy and mounding plant habit.
2. Vigorous growth habit and moderately rapid growth rate.
3. Freely branching habit; pruning is typically not required.
4. Flexible lateral branches that are resistant to cracking and splitting (breaking) at the nodes.

5. Bright green-colored developing leaves becoming dark green with development.
6. Good winter hardiness.
7. Resistant to Boxwood leaf miners, psyllids and mites.

Plants of the new *Buxus* differ primarily from plants of the parent, 'Kingsville', in the following characteristics:

1. Plants of the new *Buxus* are billowy and outwardly spreading whereas plants of 'Kingsville' are dense and congested which exacerbates susceptibility to pathogen and pest problems.
2. Plants of the new *Buxus* are faster growing than plants of 'Kingsville'.
3. Lateral branches of plants of the new *Buxus* are flexible and resistant to cracking and splitting whereas lateral branches of plants of 'Kingsville' are rigid and prone to cracking and splitting at the nodes.

Plants of the new *Buxus* can be compared to plants of *Buxus microphylla* var. *japonica* 'Morris Dwarf', not patented. In side-by-side comparisons conducted in Seneca, S.C., plants of the new *Buxus* differed primarily from plants of 'Morris Dwarf' in the following characteristics:

1. Plants of the new *Buxus* were not as compact and globular as plants of 'Morris Dwarf'.
2. Plants of the new *Buxus* were billowy and outwardly spreading whereas plants of 'Morris Dwarf' were dense and congested which exacerbates susceptibility to pathogen and pest problems.
3. Plants of the new *Buxus* were more vigorous and grew faster than plants of 'Morris Dwarf'.
4. Lateral branches of plants of the new *Buxus* were flexible and resistant to cracking and splitting whereas lateral branches of plants of 'Morris Dwarf' were rigid and prone to cracking and splitting at the nodes.
5. Plants of the new *Buxus* were more winter hardy than plants of 'Morris Dwarf'.

BRIEF DESCRIPTION OF THE PHOTOGRAPH

The accompanying colored photograph illustrates the overall appearance of the new *Buxus* plant showing the colors as true as it is reasonably possible to obtain in colored reproductions of this type. Colors in the photograph may differ slightly from the color values cited in the detailed botanical description which accurately describe the colors of the new *Buxus* plant.

The photograph comprises a side perspective view of a typical plant of 'RLH-BI' grown in an outdoor nursery.

DETAILED BOTANICAL DESCRIPTION

The aforementioned photograph and following observations, measurements and values describe plants grown during the summer under partial and full sun conditions in an outdoor nursery in Seneca, S.C. During the production of the plants, day temperatures ranged from −5° C. to 45° C. and night temperatures ranged from −25° C. to 35° C. Plants were 16 years old when the photograph and description were taken. In the following description, color references are made to The Royal Horticultural Society Colour Chart, 2007 Edition, except where general terms of ordinary dictionary significance are used.

Botanical classification: *Buxus microphylla* var. *koreana* *'RLH-BI'*.

Parentage: Naturally-occurring branch mutation of *Buxus microphylla* var. *koreana* 'Kingsville', not patented.

Propagation:

*Type.*—By semi-hardwood and hardwood cuttings.

*Time to initiate roots, summer.*—About 10 to 14 days at 27° C. to 30° C.

*Time to initiate roots, winter.*—About 18 to 25 days at 16° C. to 17° C.

*Time to produce a rooted young plant, summer.*—About 45 to 60 days at 27° C. to 30° C.

*Time to produce a rooted young plant, winter.*—About 60 to 80 days at 16° C. to 17° C.

*Root description.*—Medium in thickness to thick; fibrous, coarse and cord-like; color, close to NN155C becoming closer to 164D with development.

*Rooting habit.*—Freely branching; abundant, dense.

Plant description:

*Plant and growth habit.*—Evergreen shrub with compact, outwardly spreading to decumbent, billowy to mounding and uniform plant habit; vigorous growth habit and moderately rapid growth rate.

*Branching habit.*—Freely branching habit; bushy appearance; typically two to five lateral branches develop each spring and summer; pruning is typically not required.

*Plant height.*—About 60 cm.

*Plant width (spread).*—About 120 cm.

Lateral branch description:

*Length.*—About 1.5 cm to 3.5 cm.

*Diameter.*—About 7 mm to 10 mm.

*Internode length.*—About 5 mm to 25 mm.

*Strength.*—Strong and flexible rending the plants resistant to cracking and splitting (breaking) at the nodes.

*Texture.*—Smooth; glabrous.

*Color, developing stems.*—Close to 137D.

*Color, developed stems.*—Close to 199D.

Leaf description:

*Arrangement.*—Opposite, simple.

*Aspect.*—Mostly upright.

*Length.*—About 1.2 cm to 2.6 cm.

*Width.*—About 4 mm to 12 mm.

*Shape.*—Obovate to oblanceolate.

*Apex.*—Obtuse or aristulate.

*Base.*—Attenuate.

*Margin.*—Entire.

*Texture, upper surface.*—Smooth; mostly glabrous, proximal end of mid-vein, sparsely lanulose.

*Texture, lower surface.*—Coriaceous; glabrous.

*Venation pattern.*—Pinnate, reticulate.

*Color.*—Developing leaves, upper surface: Close to 138A. Developing leaves, lower surface: Close to 139C. Fully expanded leaves, upper surface: Close to 137A; venation, close to 137A. Fully expanded leaves, lower surface: Close to 144A; venation, close to 139D.

*Petiole.*—Length: About 1.2 mm to 1.5 mm. Diameter: About 0.4 mm to 1.1 mm. Texture, upper surface: Coriaceous; sparsely pubescent. Texture, lower surface: Coriaceous; glabrous. Color, upper surface: Close to 137A. Color, lower surface: Close to 139D.

Flower description: Flower initiation and development has not been observed on plants of the new *Buxus*.

Disease & pest resistance: Plants of the new *Buxus* have been observed to be resistant to Boxwood leaf miners, psyllids and mites. Additionally, the billowy and spreading plant habit of the new *Buxus* lends to tolerance to pathogens common to *Buxus* plants.

Landscape performance: Plant of the new *Buxus* have been observed to have excellent landscape performance and to tolerate wind, rain and temperatures ranging from about −25° C. to about 45° C.

It is claimed:

1. A new and distinct *Buxus* plant named 'RLH-BI' as illustrated and described.

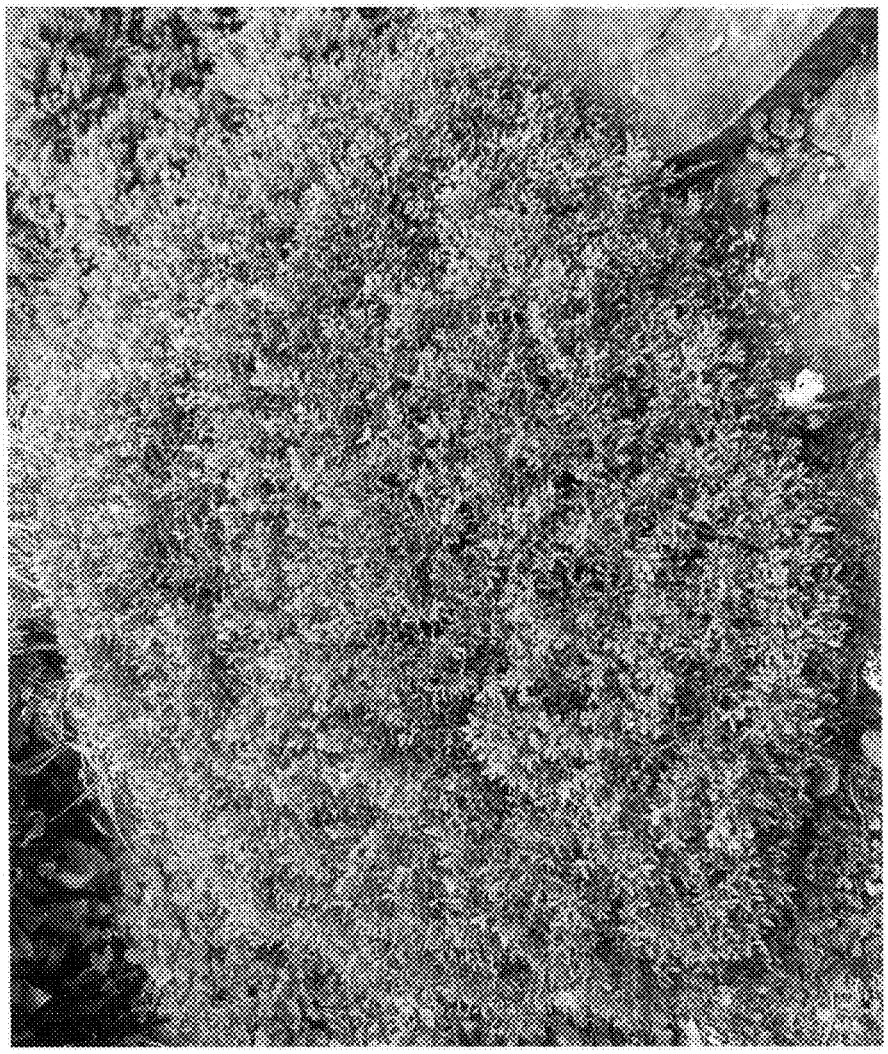

* * * * *